(12) United States Patent
Mato et al.

(10) Patent No.: US 11,666,732 B2
(45) Date of Patent: Jun. 6, 2023

(54) CATHETER DEVICE

(71) Applicant: Takashi Mato, Tokyo (JP)

(72) Inventors: Takashi Mato, Tokyo (JP); Hideki Kamimura, Tokyo (JP); Katsuya Nagai, Tokyo (JP); Kaoru Soeta, Tokyo (JP); Takeki Uozumi, Tokyo (JP)

(73) Assignee: Takashi Mato, Tokyo (JP)

( * ) Notice: Subject to any disclaimer, the term of this patent is extended or adjusted under 35 U.S.C. 154(b) by 446 days.

(21) Appl. No.: 16/612,351

(22) PCT Filed: May 8, 2018

(86) PCT No.: PCT/JP2018/017706
§ 371 (c)(1),
(2) Date: Feb. 20, 2020

(87) PCT Pub. No.: WO2018/207752
PCT Pub. Date: Nov. 15, 2018

(65) Prior Publication Data
US 2020/0206460 A1 Jul. 2, 2020

(30) Foreign Application Priority Data
May 11, 2017 (JP) .............................. JP2017-094886

(51) Int. Cl.
*A61M 25/01* (2006.01)
*A61M 25/00* (2006.01)
*A61M 39/02* (2006.01)

(52) U.S. Cl.
CPC ........ *A61M 25/01* (2013.01); *A61M 25/0067* (2013.01); *A61M 39/0247* (2013.01);
(Continued)

(58) Field of Classification Search
CPC .... A61J 15/0003; A61J 15/00; A61J 15/0088; A61M 2039/0273; A61M 2205/052;
(Continued)

(56) References Cited

U.S. PATENT DOCUMENTS 7,992,573 B2 * 8/2011 Wilson ..................... A61B 5/06
600/407
2006/0149129 A1 7/2006 Watts et al.
(Continued)

FOREIGN PATENT DOCUMENTS

JP 2002-263054 A 9/2002
JP 2007-222388 A 9/2007
(Continued)

OTHER PUBLICATIONS

International Search Report in PCT/JP2018/017706, dated Jul. 3, 2018, 4pp.

*Primary Examiner* — Brandy S Lee
(74) *Attorney, Agent, or Firm* — Hauptman Ham, LLP

(57) ABSTRACT

A catheter device according to one aspect of the present invention includes: a tube to be inserted into a body; a light emitting unit, which is provided on a distal end side of the tube, and includes an infrared light emitting element configured to emit infrared light for verifying a position of the tube; a power supply line configured to supply electric power to the infrared light emitting element; and a conduction detection unit including a visible light emitting element configured to notify a conduction state between the power supply line and the infrared light emitting element by means of visible light. With the catheter device, operation of the light emitting unit can be visually checked before inserting the tube.

6 Claims, 3 Drawing Sheets

(52) U.S. Cl.
CPC .............. *A61M 2039/0273* (2013.01); *A61M 2205/052* (2013.01); *A61M 2205/3538* (2013.01); *A61M 2205/587* (2013.01)

(58) Field of Classification Search
CPC .... A61M 2205/3538; A61M 2205/587; A61M 25/00; A61M 25/0067; A61M 25/01; A61M 39/0247; A61M 2025/0008; A61M 25/0068; A61M 25/0105
See application file for complete search history.

(56) References Cited

U.S. PATENT DOCUMENTS

2010/0016699 A1* 1/2010 Wadhawan ........ A61B 5/14546
600/361
2014/0333742 A1 11/2014 Salman et al.

FOREIGN PATENT DOCUMENTS

| | | |
|---|---|---|
| JP | 2008-526360 A | 7/2008 |
| JP | 2010-51440 A | 3/2010 |
| JP | 2013-196644 A | 9/2013 |
| JP | 2015-188674 A | 11/2015 |
| JP | 2016-87091 A | 5/2016 |
| JP | 2016-522717 A | 8/2016 |
| WO | 2015/133119 A1 | 9/2015 |

* cited by examiner

CATHETER DEVICE

RELATED APPLICATIONS

The present application is a National Phase entry of International Application No. PCT/JP2018/017706, filed May 8, 2018, which claims priority of Japanese Application No. 2017-094886, filed May 11, 2017.

TECHNICAL FIELD

This invention relates to a catheter device, and more particularly, to a catheter device including a light emitting unit for grasping a position of a distal end of a tube to be inserted into a body.

BACKGROUND ART

A tube feeding catheter device is used to feed nutrients and medicines to the stomach of a patient who cannot eat or drink by himself/herself due to disturbance of consciousness or reduced muscle force. In a method using this catheter device, a tube is inserted into the body through the mouth or the nose to reach the stomach, and the nutrients are fed to the stomach from outside the body through the tube. Although there is a risk of deteriorated abilities of the digestive system including the stomach and the intestines with only intravenous drip, when the nutrients are directly fed to the stomach through the tube, there is an advantage in that the deterioration of the abilities of the digestive system can be suppressed.

With the above-mentioned method using the catheter device, it is required to pay attention so that the tube does not erroneously enter the respiratory tract. In PTL 1, there is disclosed a catheter including a plurality of visual elements. Specifically, there is disclosed a catheter system including a fixed visual element and a movable visual element, with which a user can take a plurality of images of a lesion from various angles. In the catheter system, an LED is provided at a distal end of a tube to irradiate light, to thereby increase quality of the images taken by the visual elements.

Further, in PTL 2, there is disclosed a light emitting device for an internal portion, which is to be inserted into a tubule inside a living body to emit light. This device includes a body section formed of a tubular body having both ends thereof sealed and having flexibility and optical transparency, at least one light emitting section internally provided in the body section, and light emitting means for causing the light emitting section to emit light. With the light emitting device for an internal portion, the body section is caused to emit light after being inserted into the living body while emitting light so that a doctor or a veterinarian can correctly and visually observe a position and a running state of the tubule in a laparoscopic operation, for example.

In PTL 3, there are disclosed a catheter device and a catheter position verification method, with which light is emitted to a fiber from a light source to appropriately verify a position of a distal end portion of a catheter. This device includes the catheter to be inserted into a body, a light source part including a laser diode configured to radiate visible red light, and the fiber configured to guide the visible red light radiated from the light source part to the neighborhood of the distal end portion of the catheter.

CITATION LIST

Patent Literature

[PTL 1] JP 2008-526360 A
[PTL 2] JP 2007-222388 A
[PTL 3] JP 2016-087901 A

SUMMARY OF INVENTION

Technical Problem

In a catheter device including a light emitting unit at a distal end of a tube, light having a wavelength in an infrared region, which is easily transmitted through a human body, is radiated from the light emitting unit, and hence it is hard to visually check whether the light emitting unit is lit normally. Meanwhile, it is requested by a user handling the catheter device to visually check whether the light emitting unit at the distal end of the tube is operating normally before inserting the tube into a patient.

It is an object of this invention to provide a catheter device with which operation of a light emitting unit can be visually checked before insertion of a tube.

Solution to Problem

In order to solve the above-mentioned problem, according to one aspect of this invention, there is provided a catheter device including: a tube to be inserted into a body; a light emitting unit, which is provided on a distal end side of the tube, and includes an infrared light emitting element configured to emit infrared light for verifying a position of the tube; a power supply line configured to supply electric power to the infrared light emitting element; and a conduction detection unit including a visible light emitting element configured to notify a conduction state between the power supply line and the infrared light emitting element by means of visible light.

With the above-mentioned configuration, it is possible to verify, based on a state of the visible light emitted from the visible light emitting element of the conduction detection unit, the conduction state between the infrared light emitting element of the light emitting unit provided on the distal end side of the tube, and the power supply line configured to supply electric power to the infrared light emitting element.

In the above-mentioned catheter device, the light emitting unit may include a base extending in a lead-out direction of the tube, and the infrared light emitting element and the visible light emitting element may be mounted on the base. With this configuration, with the visible light emitting element of the conduction detection unit being provided at the position of the light emitting unit provided on the distal end side of the tube, a light emitting state of the visible light for verifying the conduction can be checked on the distal end side of the tube.

In the above-mentioned catheter device, the visible light emitting element may be arranged side by side with the infrared light emitting element in the lead-out direction. With this configuration, even when the infrared light emitting element and the visible light emitting element are provided on the distal end side of the tube, it is possible to prevent an external diameter on the distal end side of the tube from being increased more than necessary.

In the above-mentioned catheter device, the visible light emitting element may be provided in middle of the tube, and the visible light emitting element may be provided on a trailing end side of the tube. With this configuration, the light emitting state of the visible light can be checked even when the distal end side of the tube is inserted into a human body.

In the above-mentioned catheter device, the catheter device may further include a connector portion provided on a trailing end side of the tube to connect the tube and an external device, and the visible light emitting element may be provided in the connector portion. With this configuration, it is possible to verify, based on the light emitting state of the visible light, the conduction state between the infrared light emitting element and the power supply line at the position of the connector portion provided on the trailing end side of the tube.

The above-mentioned catheter device may further include: a bypass line, which is provided in parallel to the power supply line, and is configured to bypass the visible light emitting element and supply electric power to the infrared light emitting element; and a switch unit configured to switch a line for supplying electric power to the infrared light emitting element between the power supply line and the bypass line. With this configuration, after the conduction state between the infrared light emitting element and the power supply line is verified based on the light emitting state of the visible light emitting element, the visible light emitting element can be prevented from emitting light through the switching to the bypass line. Specifically, after the conduction state between the infrared light emitting element and the power supply line is verified, the visible light emitting element is prevented from emitting light to reduce electric power consumption and prevent heat generation.

Effect of Invention

According to this invention, the catheter device with which operation of the light emitting unit can be visually verified before inserting the tube can be provided.

BEST MODE FOR CARRYING OUT THE INVENTION

Now, an embodiment of this invention is described with reference to the drawings. In the following description, like members are denoted by like reference symbols, and a description on members once described is omitted as appropriate.

(Configuration of Catheter Device)

Figure 1:
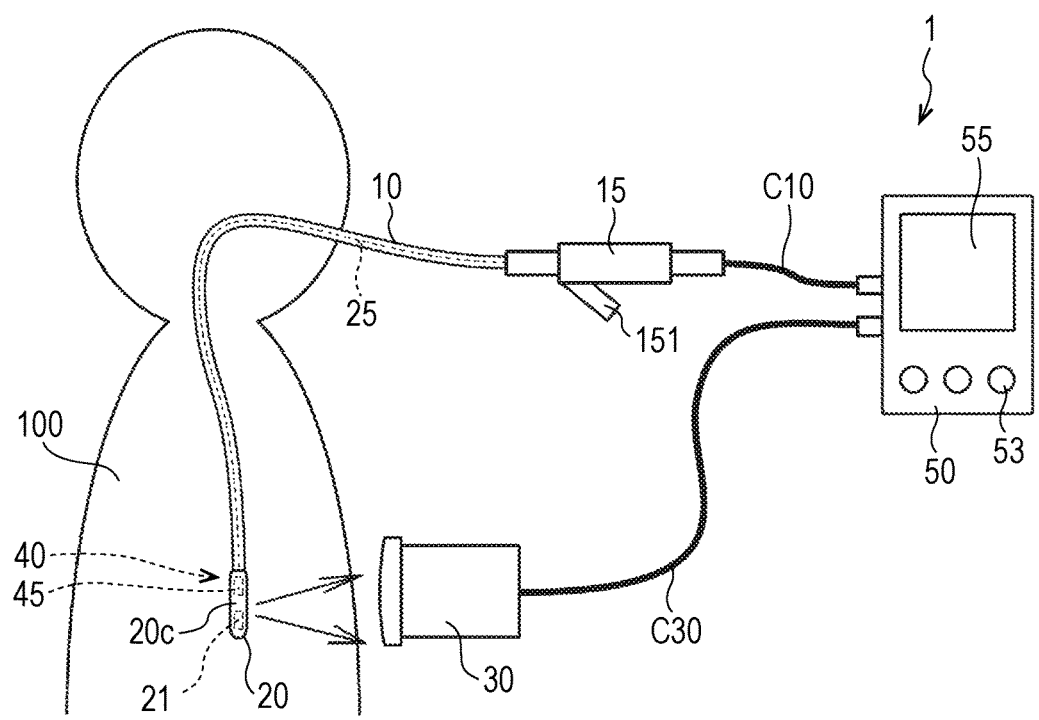
FIG. 1 is a schematic diagram for illustrating a catheter device according to an embodiment of this invention.

FIG. 1 is a schematic diagram for illustrating a catheter device according to this embodiment.

A catheter device 1 according to this embodiment includes a tube 10 to be inserted into a human body 100, a light emitting unit 20 provided on a distal end side of the tube 10, a power supply line 25, and a conduction detection unit 40 including a visible light emitting element 45. The catheter device 1 illustrated in FIG. 1 further includes a light receiving unit 30 and a control unit 50. As an example, the catheter device 1 inserts the tube 10 into the body through the mouth or the nose until a distal end of the tube 10 reaches the stomach through the gullet. Then, nutrients and medicines are fed to the stomach from outside the body through the tube 10. As a result, the nutrients and the medicines can be directly fed to the stomach of a patient.

A connector 15 (connector portion) is connected to a trailing end side of the tube 10, and a cable C10 is connected to the connector 15. The cable C10 is connected to the control unit 50 (external device). The power supply line 25 is provided in the tube 10, and the power supply line 25 has one end thereof connected to the light emitting unit 20, and another end thereof connected to the connector 15. The connector 15 plays a role of establishing conduction between the power supply line 25 of the tube 10 and the cable C10.

The connector 15 also includes a feeding port 151 communicating to a port on the other end side (port outside the body) of the tube 10. The nutrients and the medicines can be fed into the tube 10 through the feeding port 151.

The light emitting unit 20 includes an infrared light emitting element 21 to be used to verify a position of the tube 10. Infrared light emitted from the infrared light emitting element 21 has a wavelength of from about 650 nm to about 1,000 nm, for example, and can be transmitted through the human body 100. Therefore, when the tube 10 is inserted into the body, the infrared light radiated from the light emitting unit 20 provided on the distal end side of the tube 10 can be received outside the body. The power supply line 25 is connected to the infrared light emitting element 21. The power supply line 25 is embedded in a wall (thickness) of the tube 10, for example, and extends from the distal end to a trailing end of the tube 10.

Further, the light emitting unit 20 is protected by a cap 20c. Water can be prevented from entering the inside of the light emitting unit 20 by the cap 20c, and operability in inserting the tube 10 into the human body 100 is increased by a smooth outer shape of the cap 20c.

The light receiving unit 30 is a portion configured to receive the infrared light that has been radiated from the light emitting unit 20 and transmitted through the human body 100. The light receiving unit 30 is arranged at a position near the human body 100 and outside the body. For example, when it is desired that the distal end of the tube 10 reach the stomach, the light receiving unit 30 is arranged near the stomach and outside the body. The light receiving unit 30 is connected to the control unit 50 via a cable C30. An electric signal based on the infrared light received by the light receiving unit 30 is sent to the control unit 50 through the cable C30.

The control unit 50 is a portion configured to control the light emitting unit 20, the light receiving unit 30, and other units. The control unit 50 includes operation buttons 53 and a display 55. The control unit 50 is configured to control and energize the light emitting unit 20 via the cable C10. Specifically, electric power required for the light emitting unit 20 to operate is supplied from the control unit 50 to the infrared light emitting element 21 of the light emitting unit 20 through the cable C10 and the power supply line 25 inside the tube 10.

The display 55 is configured to display results of detection by the light receiving unit 30. For example, when the signal based on an intensity of the infrared light detected by the light receiving unit 30 exceeds a predetermined value, a message indicating the "detection" is displayed. Moreover, a numerical value, a graph, or a picture corresponding to the signal intensity may be displayed. The control unit 50 may notify the message of "detection" by means of a sound. The operation buttons 53 are used to switch display on the display 55 and change settings, for example.

The conduction detection unit 40 is a portion configured to detect a conduction state between the power supply line 25 and the infrared light emitting element 21. The visible light emitting element 45 included in the conduction detection unit 40 notifies the conduction state between the power supply line 25 and the infrared light emitting element 21 by means of visible light. In the example illustrated in FIG. 1, the visible light emitting element 45 is provided in the light emitting unit 20. When the power supply line 25 and the infrared light emitting element 21 are in the conduction state, the visible light is radiated from the visible light emitting element 45.

In contrast, when the power supply line 25 and the infrared light emitting element 21 are not in the conduction state, no visible light is radiated from the visible light emitting element 45. The infrared light, which is hard to visually recognize, is radiated by the infrared light emitting element 21, and hence it is difficult to grasp whether the operation is performed normally. Therefore, it becomes easy to visually verify the conduction state between the power supply line 25 and the infrared light emitting element 21 depending on whether the visible light is radiated from the visible light emitting element 45.

When the catheter device 1 is to be used, the tube 10 and the connector 15 are connected to each other first, and the cable C10 is connected to the connector 15 to be connected to the control unit 50. Further, the light receiving unit 30 is connected to the control unit 50 through the cable C30.

Next, electric power is supplied to the light emitting unit 20 from the control unit 50 through the cable C10 and the wiring of the tube 10 to radiate the infrared light. At this time, when electric power is normally supplied from the power supply line 25 to the infrared light emitting element 21, the visible light is radiated from the visible light emitting element 45 of the conduction detection unit 40. A user can check whether the infrared light is normally radiated from the infrared light emitting element 21 based on a light emitting state of the visible light emitting element 45.

After it is verified that the infrared light emitting element 21 is operating normally based on the visible light radiated from the visible light emitting element 45, the tube 10 is inserted into the body via the mouth or the nose under this state. Meanwhile, the light receiving unit 30 is arranged in advance outside the body and near the position to which the distal end of the tube 10 is desired to reach. For example, when the tube 10 is desired to be inserted to the stomach, the light receiving unit 30 is arranged in advance outside the body and near the stomach (near the upper abdomen).

The tube 10 is inserted into the body under this state. Then, when the distal end of the tube 10 reaches the stomach, the infrared light radiated from the light emitting unit 20 is transmitted through the human body 100 to reach the light receiving unit 30. When the light receiving unit 30 receives the infrared light, a signal corresponding to an amount of the light is sent to the control unit 50 through the cable C30. When the signal exceeds a preset value, a message of reaching is displayed on the display 55 of the control unit 50.

In contrast, when the distal end of the tube 10 has not reached the stomach, the amount of the infrared light received by the light receiving unit 30 is small, and hence the message of reaching is not displayed on the display 55. As a result, the user can recognize whether the distal end of the tube 10 has reached the stomach based on the display on the display 55.

In the example described above, the position of the distal end is detected while the tube 10 is inserted into the body. However, when markings indicating lengths from the distal end are provided on the tube 10, the tube 10 may be inserted into the body with reference to the markings, and the light receiving unit 30 may be placed for detection after the tube is inserted up to a target length.

(Configuration Example of Light Emitting Unit)

Figure 2:
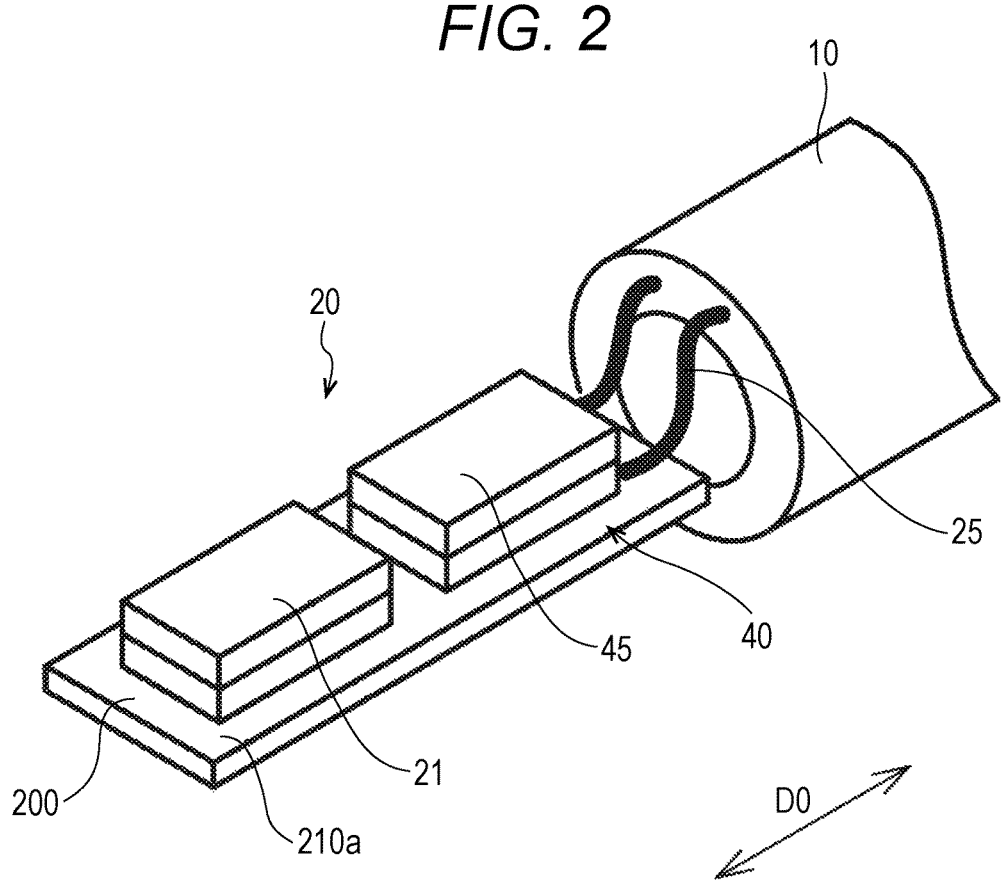
FIG. 2 is a perspective view for illustrating a configuration example of a light emitting unit.

FIG. 2 is a perspective view for illustrating a configuration example of the light emitting unit. In FIG. 2, the cap 20c is omitted for convenience of description. The light emitting unit 20 includes a substrate 200, which is a base extending in a lead-out direction D0 of the tube 10, and the infrared light emitting element 21 mounted on the substrate 200. The "lead-out direction D0 of the tube 10" as used herein refers to a direction in which the tube 10 extends when the tube 10 is straightened.

The substrate 200 is a flexible substrate on which a wiring pattern is formed, for example. The infrared light emitting element 21 is mounted on a mounting surface 210a of the substrate 200. The visible light emitting element 45 of the conduction detection unit 40 is also mounted on the mounting surface 210a. The visible light emitting element 45 is arranged side by side with the infrared light emitting element 21 in the lead-out direction D0 on the mounting surface 210a.

On the substrate 200, the infrared light emitting element 21 and the visible light emitting element 45 are mounted to establish conduction to the wiring pattern. Further, the power supply line 25 led out from the tube 10 is connected to the wiring pattern, and electric power is supplied to the infrared light emitting element 21 and the visible light emitting element 45 from the power supply line 25 through the wiring pattern.

In such a light emitting unit 20, with the infrared light emitting element 21 and the visible light emitting element 45 being arranged side by side on the mounting surface 210a of the substrate 200, the operation can be verified by means of the visible light at a position near the infrared light emitting element 21, which is desired to be verified for operation. The operation can be verified at the position near the target to be verified for operation, and hence the operation can be verified intuitively.

Figure 3:
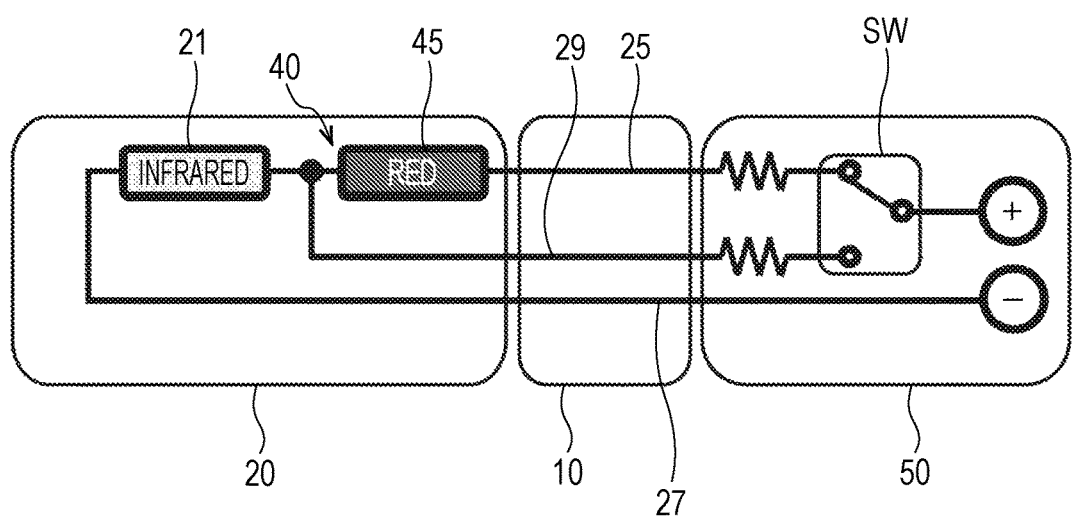
FIG. 3 is a diagram for illustrating a circuit configuration (No. 1) of a conduction detection unit.

FIG. 3 is a diagram for illustrating a circuit configuration (No. 1) of the conduction detection unit.

In FIG. 3, for convenience of description, the light emitting unit 20, the tube 10, and the control unit 50 are illustrated. In this circuit configuration, the power supply line 25, a bypass line 29, and a ground line 27 are provided between the control unit 50 and the light emitting unit 20. The three wirings of the power supply line 25, the bypass line 29, and the ground line 27 are provided in parallel along the tube 10.

In the light emitting unit 20, the infrared light emitting element 21 and the visible light emitting element 45 are connected in series between the power supply line 25 and the ground line 27. The control unit 50 includes a switch unit SW. The switch unit SW is configured to perform switching as to whether one side (for example, positive side) of a power source is connected to the power supply line 25 or the bypass line 29.

The bypass line 29 is provided in parallel to the power supply line 25, and is a line (power supply line) configured to bypass the visible light emitting element 45 and supply electric power to the infrared light emitting element 21. Therefore, when the power supply line 25 is selected by the switch unit SW, electric power is supplied to the infrared light emitting element 21 and the visible light emitting element 45, and when the bypass line 29 is selected, the electric power is supplied to the infrared light emitting element 21 while bypassing the visible light emitting element 45.

In such a circuit configuration, when the conduction state between the infrared light emitting element 21 and the power supply line 25 is to be verified, the power supply line 25 is selected by the switch unit SW, and the operation of the infrared light emitting element 21 is verified based on the light emitting state of the visible light emitting element 45 connected in series to the infrared light emitting element 21. Then, after the operation is verified, the bypass line 29 is selected by the switch unit SW, and only the infrared light emitting element 21 is allowed to emit light while no electric power is supplied to the visible light emitting element 45. With this configuration, after the conduction state between the infrared light emitting element 21 and the power supply line 25 has been verified, the visible light emitting element 45 can be prevented from emitting light, to thereby suppress electric power consumption and prevent heat generation.

Figure 4:
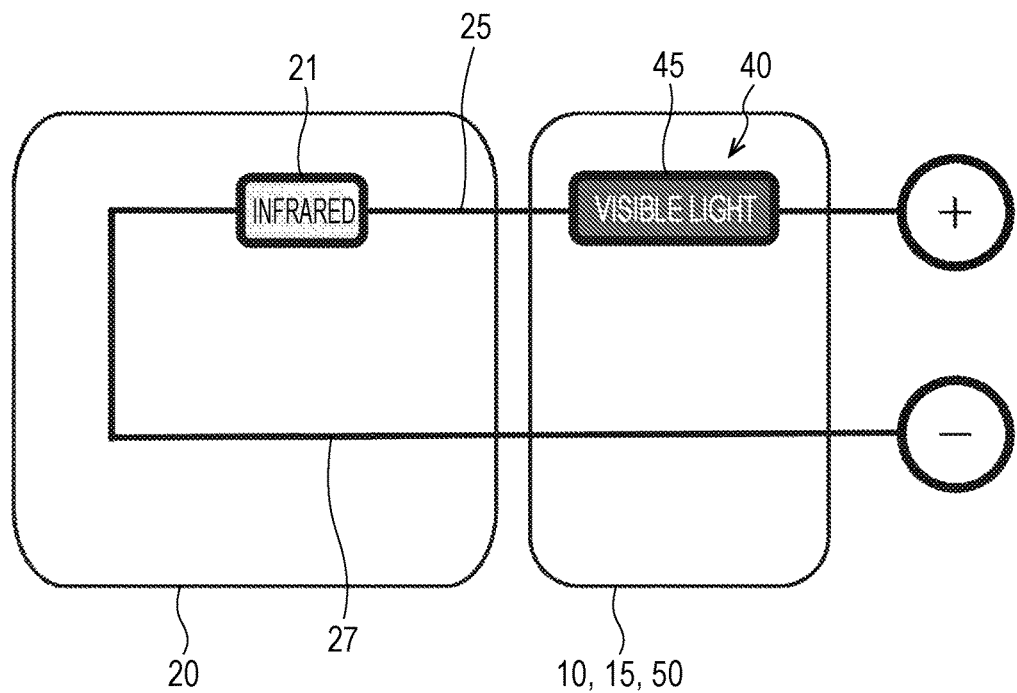
FIG. 4 is a diagram for illustrating a circuit configuration (No. 2) of the conduction detection unit.

FIG. 4 is a diagram for illustrating a circuit configuration (No. 2) of the conduction detection unit. In this circuit configuration, the infrared light emitting element 21 and the visible light emitting element 45 are connected in series to the power supply line 25, and the visible light emitting element 45 is provided at a position other than the light emitting unit 20. The light emitting unit 20 includes the infrared light emitting element 21, which is connected in series to the power supply line 25. The visible light emitting element 45 provided at the position other than the light emitting unit 20 is also connected in series to the infrared light emitting element 21, and is connected to the power supply line 25.

Therefore, through supply of electric power to the power supply line 25, when the conduction state is normal, light is radiated from the infrared light emitting element 21 and the visible light emitting element 45. In contrast, when the conduction state is abnormal, light is not radiated from the infrared light emitting element 21 and the visible light emitting element 45. Therefore, the user can verify the conduction state between the infrared light emitting element 21 and the power supply line 25 based on whether the visible light is radiated from the visible light emitting element 45 when electric power is supplied to the power supply line 25.

Figure 5:
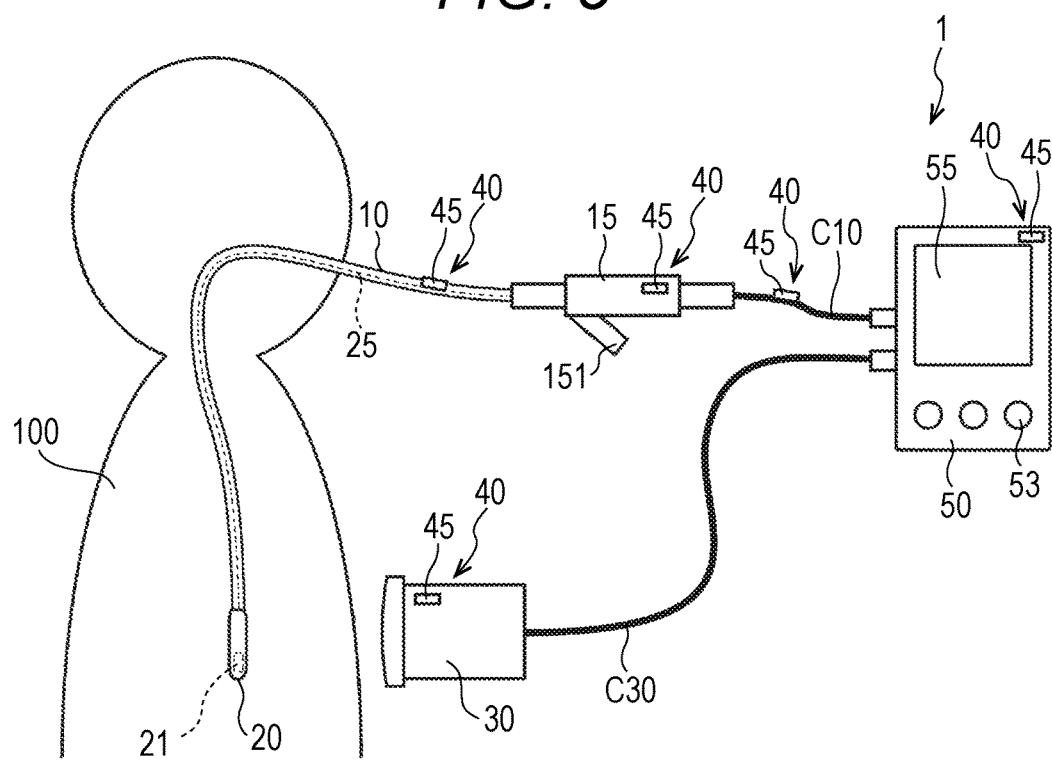
FIG. 5 is a schematic diagram for illustrating arrangement examples of a visible light emitting element.

FIG. 5 is a schematic diagram for illustrating arrangement examples of the visible light emitting element.

In FIG. 5, examples in which the visible light emitting element 45 is arranged at a position other than the light emitting unit 20 are illustrated. The visible light emitting element 45 can be arranged at a position that can be easily seen, for example, in middle of the tube 10, at a position of the connector 15, in middle of the cable C10, at a position of the control unit 50, or at a position of the light receiving unit 30. The visible light emitting element 45 may be arranged at any position as long as the visible light is radiated depending on the conduction state between the infrared light emitting element 21 and the power supply line 25. It is only required that the visible light emitting element 45 be provided at a position that can be easily checked by the user.

The embodiments have been described above, but this invention is not limited to those examples. For example, in the embodiment described above, there has been described the circuit configuration in which the visible light is radiated from the visible light emitting element 45 when the conduction state between the infrared light emitting element 21 and the power supply line 25 is normal, and the visible light is not radiated when the conduction state is abnormal. However, to the contrary, there may be adopted a circuit configuration in which the visible light is not radiated from the visible light emitting element 45 when the conduction state is normal, and the visible light is radiated when the conduction state is abnormal. Further, there has been described the example in which the visible light is radiated from the visible light emitting element 45 as the conduction detection unit 40, but the conduction state between the infrared light emitting element 21 and the power supply line 25 may be notified on the display 55 of the control unit 50.

Further, in the embodiment described above, there has been described the example in which the tube 10 is inserted into the body through the mouth or the nose, but this invention is also applicable to a case in which the tube 10 is inserted through the anus or a hole formed in the body by a procedure. Further, there has been described, as the light emitting unit 20, the example in which the infrared light emitting element 21 and the visible light emitting element 45 are arranged side by side in the lead-out direction D0, but the infrared light emitting element 21 and the visible light emitting element 45 may be mounted on the front and the back of the substrate 200, respectively.

Further, this invention encompasses any addition, deletion, and change in design of components that may be made to the embodiments described above by those skilled in the art, or any appropriate combination of features of the embodiments without departing from the gist of this invention.

REFERENCE SIGNS LIST

1 . . . catheter device
10 . . . tube
15 . . . connector
20 . . . light emitting unit
20c . . . cap
21 . . . infrared light emitting element
25 . . . power supply line
27 . . . ground line
29 . . . bypass line
30 . . . light receiving unit
40 . . . conduction detection unit
45 . . . visible light emitting element
50 . . . control unit
53 . . . operation button
55 . . . display
100 . . . human body
151 . . . feeding port
200 . . . substrate
210a . . . mounting surface
C10 . . . cable
C30 . . . cable
D0 . . . lead-out direction
SW . . . switch unit

The invention claimed is:

1. A catheter device, comprising:
    a tube to be inserted into a body;
    a light emitting unit, which is provided on a distal end side of the tube, and includes an infrared light emitting element configured to emit infrared light for verifying a position of the tube;
    a power supply line configured to supply electric power to the infrared light emitting element;
    a conduction detection unit including a visible light emitting element configured to notify a conduction state between the power supply line and the infrared light emitting element by means of visible light; and
    a connector portion provided at a trailing end side of the tube opposite to the distal end side of the tube, wherein the infrared light emitting element and the visible light emitting element are disposed at the distal end side of the tube and configured to be inserted into the body while the connector portion is outside the body.

2. The catheter device according to claim 1,
    wherein the light emitting unit includes a base extending in a lead-out direction of the tube, and
    wherein the infrared light emitting element and the visible light emitting element are mounted on the base.

3. The catheter device according to claim 2, wherein the visible light emitting element is arranged side by side with the infrared light emitting element in the lead-out direction.

4. The catheter device according to claim 1, wherein the connector portion connects the tube to an external device.

5. The catheter device according to claim 1, further comprising:
    a bypass line, which is provided in parallel to the power supply line, and is configured to bypass the visible light emitting element and supply electric power to the infrared light emitting element; and
    a switch unit configured to switch a line for supplying electric power to the infrared light emitting element between the power supply line and the bypass line.

6. The catheter device according to claim 1, further comprising a light receiving unit configured to receive the infrared light radiated from the light emitting unit.

* * * * *